(12) United States Patent
Jin et al.

(10) Patent No.: US 8,658,000 B2
(45) Date of Patent: Feb. 25, 2014

(54) PREPARATION METHOD OF APIGENIN AND DEHYDROSILYBIN MIXTURE USING RADIATION

(71) Applicant: Korea Atomic Energy Research Institute, Daejeon (KR)

(72) Inventors: Chang Hyun Jin, Jeollabuk-do (KR); Il Yun Jeong, Jeollabuk-do (KR); Hyung-Won Ryu, Gyeongsangnam-do (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 13/667,894

(22) Filed: Nov. 2, 2012

(65) Prior Publication Data
US 2013/0146440 A1    Jun. 13, 2013

(30) Foreign Application Priority Data
Dec. 9, 2011    (KR) ........................ 10-2011-0131687

(51) Int. Cl.
*B01J 19/12*    (2006.01)
*B01J 19/08*    (2006.01)
*C07D 311/30*    (2006.01)

(52) U.S. Cl.
USPC ................................ 204/157.69; 204/157.65

(58) Field of Classification Search
USPC ........................ 204/157.69, 157.65
See application file for complete search history.

(56) References Cited

U.S. PATENT DOCUMENTS

| | | | |
|---|---|---|---|
| 6,682,695 B2 * | 1/2004 | MacPhee et al. | 422/22 |
| 8,569,358 B2 * | 10/2013 | Bernard et al. | 514/452 |
| 2001/0047032 A1 * | 11/2001 | Castillo et al. | 514/453 |
| 2004/0225004 A1 * | 11/2004 | Zeligs | 514/419 |
| 2008/0200538 A1 * | 8/2008 | Doseff et al. | 514/456 |
| 2008/0213217 A1 * | 9/2008 | Storer et al. | 514/80 |
| 2011/0021614 A1 * | 1/2011 | Cheng et al. | 514/452 |
| 2011/0116968 A1 * | 5/2011 | Brunner et al. | 422/22 |

FOREIGN PATENT DOCUMENTS

KR    10-0437274    6/2004

OTHER PUBLICATIONS

Fu et al, "Protective Effects of silybin and analogues against X-ray radiation-induced damage," Acta Biochim. Biophys. Sin. 2010, vol. 42, pp. 489-495.*
Fu et al, "Free radical scavenging reactions and antioxidant activities of silybin: Mechanistic aspects and pulse radiolytic studies," Free Radical Research, Sep. 2009, vol. 43, No. 9, pp. 887-897.*
Fu et al, "Laser photolysis and pulse radiolysis studies on silybin in ethanol solutions," Rad. Phys. and Chem., vol. 77 (2008), pp. 1300-1305.*

(Continued)

*Primary Examiner* — Keith Hendricks
*Assistant Examiner* — Colleen M Raphael
(74) *Attorney, Agent, or Firm* — Lathrop & Gage LLP

(57) ABSTRACT

A preparation method of chromenone derivatives using radiation is provided. The preparation method exposes commercially-available silybin in reaction solvent to radiation, to thereby concurrently obtain both dehydrosilybin and apigenin compounds, which are chromenone compounds, in a simple reaction step and with high yield. Because the compounds are prepared at economic cost, the preparation method can be advantageously used particularly for the purpose of mass production. Further, in consideration of good cancer cell viability suppression effect thereof, dehydrosilybin and apigenin prepared according to the preparation method can be advantageously used as a pharmaceutical composition for prevention and treatment of cancer.

13 Claims, 7 Drawing Sheets

(56) References Cited

OTHER PUBLICATIONS

Nagy et al, "Oxidation of naringenin by gamma-radiation," Rad. Phys. and Chem., vol. 77 (2008), pp. 728-733.*

Fu et al. (2008), "Laser photolysis and pulse radiolysis studies on silybin in ethanol solutions," Radiation Physics and Chemistry 77: 1300-1305.

Gažák et al. (2004), "Oxidised derivatives of silybin and their antiradical and antioxidant activity," Bioorganic & Medicinal Chemistry 12: 5677-5687.

Huber et al. (2008), "Significantly greater antioxidant anticancer activities of 2,3-dehydrosilybin than silybin", Biochemica et Biophysica Acta 1780: 837-847.

Lo et al. (2002), "Carnosol, an antioxidant in rosemary, suppresses inducible nitric oxide synthase through down-regulating nuclear factor-κB in mouse macrophages", Carcinogenesis vol. 23, No. 6, pp. 983-991.

Gupta et al. (2001), "Selective Growth-Inhibitory, Cell-Cycle Deregulatory and Apoptotic Response of Apigenin in Normal versus Human Prostate Carcinoma Cells", Biochemical and Biophysical Research Communication 287, 914-920.

Engelmann et al. (2002), "Apigenin—strong cytostatic and anti-angiogenic action in vitro contrasted by lack of efficacy in vivo", Phytomedicine 9:489-495.

Maitrejean et al. (2000), "The Flavanolignan Silybin and its Hemiynthetic Derivatives, a Novel Series of Potential Modulators of P-Glycoprotein", Bioorganic & Medicinal Letters 10: 157-160.

Chen et al. (2009), "The efficient total synthesis of bis-glycosyl apigenin from naringenin: a greener way", Carbohydrate Research 344; 2245-2249.

Plaumann et al. (1996), "Flavonoids activate wild-type p53," Oncogene 13: 1605-1614.

* cited by examiner

PREPARATION METHOD OF APIGENIN AND DEHYDROSILYBIN MIXTURE USING RADIATION

CROSS-REFERENCES TO RELATED APPLICATION

This application claims priority from Korean Patent Application No. 10-2011-0131687, filed on Dec. 9, 2011, in the Korean Intellectual Property Office, the contents of which are incorporated herein by reference in its entirety

BACKGROUND OF THE INVENTION

1. Field of the Invention

The present invention relates to a preparation method of chromenone derivatives using radiation.

2. Description of the Related Art

Silybin is major active component of a thistle of the genus *Silybum*, a flowering plant of the daisy family (Asteraceae). Milk thistle has been used popularly over approximately 2000 years to treat liver diseases in Europe and other countries.

Studies report antioxidative and anticancer effect of silybin. Both in vitro and animal research suggest that silybin has hepatoprotective (antihepatotoxic) properties that protect liver cells against toxins. Silybin has also demonstrated anticancer effects against human prostate adenocarcinoma cells, estrogen-dependent and -independent human breast carcinoma cells, human ectocervical carcinoma cells, human colon cancer cells, and human lung carcinoma cells.

Dihydrosilybin is derivative of silybin, which has antioxidative activity, UV-protective effect, and furthermore, inhibitory activity against cytochrome P450 isoform CYP1A1 in human keratinocytes (HaCaT) and human hepatoma cells (HepG2).

Further, the recent study has suggested that dehydrosilybin (DHS) has higher inhibitory effect against granulocorpuscle lipid peroxidation, along with higher cell apoptosis effect, P-glycoprotein inhibitory effect and anticancer effect than silybin (Axel Huber, et. al., Biochimica et Biophysica Acta 1780 (2008) 837-847).

Further, apigenin is known to play a regulatory role in the mechanism of iNOS, COX-2, and NFκB activation (Lo, A. H. et al., Carcinogenesis 23(6): 983-991 (2002)), but leaves COX-1 uninhibited, thus used as arthritis treatment. Apigenin is also known to have a variety of biological activities including, antiinflammation, vasorelaxatory effect, antioxidation, antiviral activity, and anticancer activity. Regarding anticancer activity, in particular, apigenin can effectively act at a low concentration below approximately 50 µM for example, and act on the mechanism of apoptosis and necrosis in the cellular proliferation and angiogenesis, the representative characteristic of various cancers such as prostate cancer, breast cancer, lung cancer, colon cancer, blood cancer (leukemia), skin cancer, thyroid cancer, and liver cancer, to induce antiproliferative and cytotoxicity effect, thereby suppressing proliferation of cancer cells.

Apigenin is also reported to exert cytotoxicity effect and proliferation suppression activity such as accumulation of tumor suppressor protein p53 and inducement of cell apoptosis in nontumor cell such as murine embryo fibroblast as well as tumor cells. Apigenin is also known to exert some proliferation suppression effect in normal human prostatic endothelial cells (Plaumann B. et al., Oncogene 13(8), 1605-14 (1996) and Gupta, S. et al., Biochem. Biophys. Res. Commun. 287(4): 914-920).

However, recent study has also reported that while excellent effect is observed in in vitro test including cell line depending on concentration of apigenin per lung carcinoma cell line and colon carcinoma cell line, little effect is observed in vivo (Engelmann, C. et al., Phyto medicine 9(6): 489-495 (2002)).

To be specific, the effect of apigenin, based on the mechanism of suppressing cellular proliferation, includes both the cell proliferation suppression and cytotoxicity, and reacts very sensitively to effect at low concentration. Use of apigenin for articular cartilage restoration (Korean Patent No. 10-0437274).

Meanwhile, both dehydrosilybin and apigen are derived from natural product. These are usually isolated from the natural product for use in bioavailability measurement. For example, dehydrosilybin is prepared from commercially-available silybin via oxidation under potassium acetate (KOAc) dissolved in iodine and acetic acid (Barron, D., et. al., Bioorg Med Chem. Lett. 2000, 10(2), 157), and apigen can be prepared from naringenin (Jianli Chen, et. al., Carbohydrate Research 344 (2009) 2245-2249).

However, in these conventional synthetic compounds, it is impossible to obtain both dehydrosilybin and apigenin compounds at the same time, and the preparation of the compounds requires various reagents which are frequently hazardous to environment and pricy.

While researching for a compound preparation method which could overcome the shortcomings of the prior art mentioned above, the present inventors confirmed that it is possible to obtain both dehydrosilybin and apigenin compounds at the same time and without having to use reagents, by exposing commercially-available silybin in reactive solvent to radiation and thus completed the present invention.

PRIOR ARTS

Patent Document

Korean Patent No. 10-0437274

Non-Patent Document

1. Axel Huber, et. al., Biochimica et Biophysica Acta 1780, 837-847 (2008)
2. Lo, A. H. et al., Carcinogenesis 23(6): 983-991 (2002)
3. Gupta, S. et al., Biochem. Biophys. Res. Commun. 287(4): 914-920
4. Engelmann, C. et al., Phyto medicine 9(6): 489-495 (2002)
5. Barron, D., et. al., Bioorg Med Chem Lett. 10(2), 157 (2000)
6. Jianli Chen, et. al., Carbohydrate Research 344, 2245-2249 (2009)

SUMMARY OF THE INVENTION

An object of the present invention is to provide a preparation method of chromenone derivatives.

In order to accomplish the above-mentioned object of the present invention, a preparation method of chromenone derivatives expressed by chemical formula 1 or 2 is provided, which includes a step of dissolving chroman compound of chemical formula 3 in a reactive solvent, and obtaining a final compound by exposing the reacted mixture to radiation:

[Reaction formula 1]

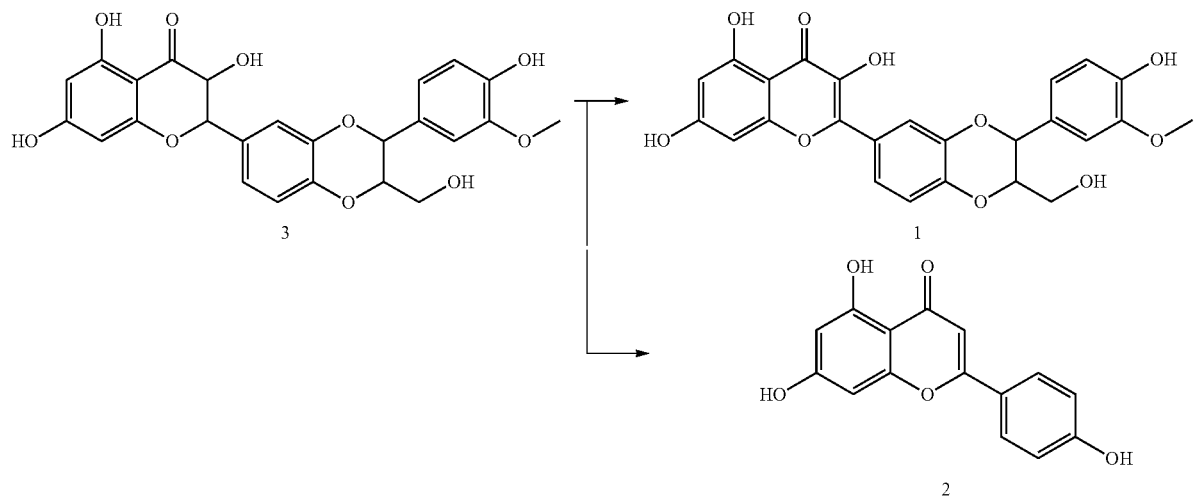

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF THE INVENTION

Figure 1:
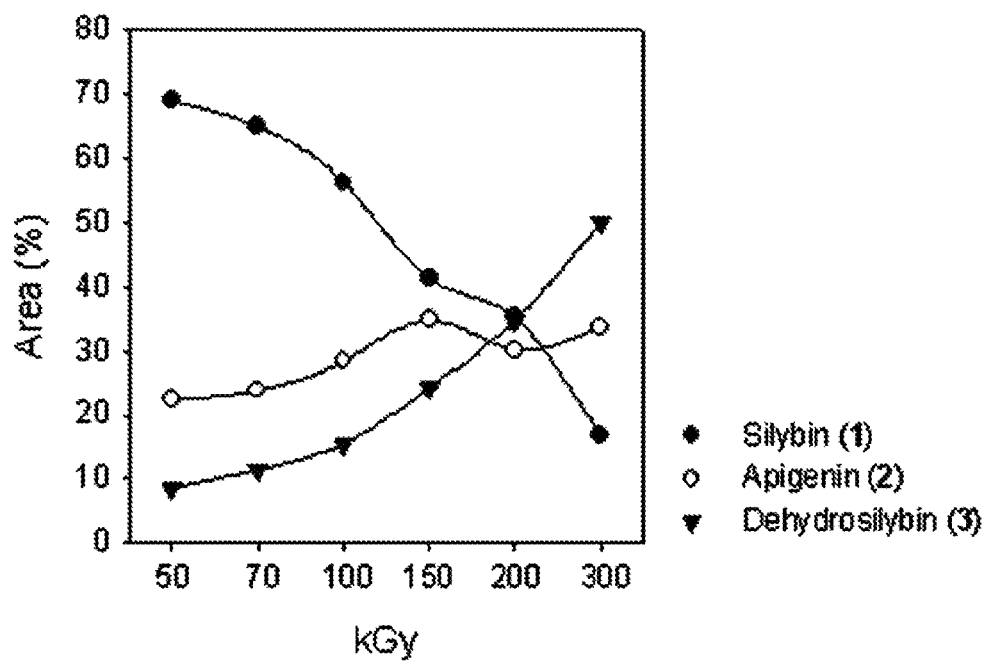
FIG. 1 illustrates transformation rate of compounds by radiation dose according to an embodiment of the present invention.

According to the present invention, a preparation method of chromenone derivatives of chemical formula 1 or 2 as expressed by Reaction Formula 1 is provided, which comprises a step of dissolving chroman compound of chemical formula 3 in a reactive solvent and obtaining a final compound by exposing the reacted mixture to radiation:

[Reaction Formula 1]

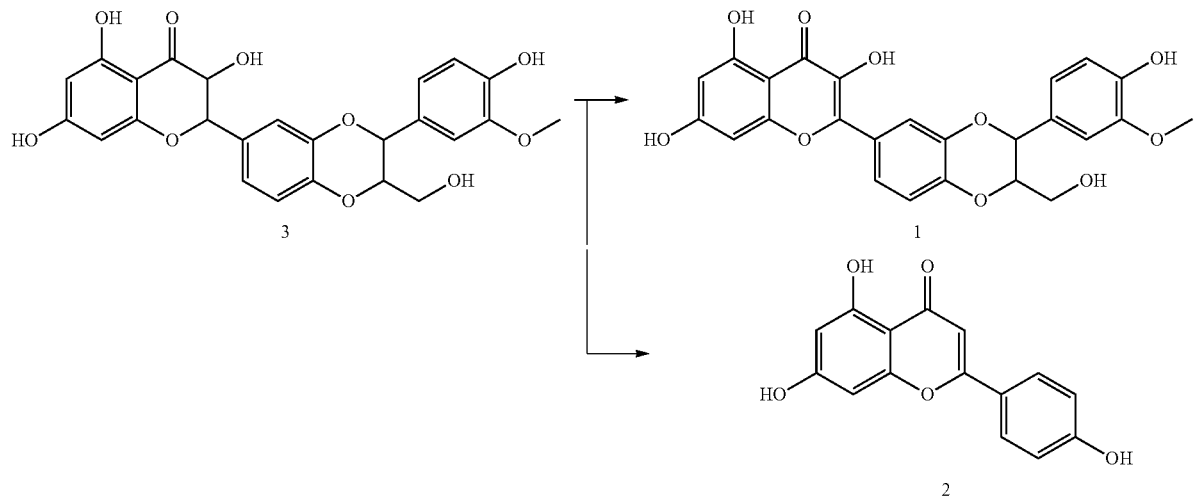

According to the present invention, the preparation method irradiates commercially-available silybin in a reactive solvent, and thus concurrently obtains both dehydrosilybin and apigenin compounds, i.e., the chromenone compounds, in a simple reaction process and with higher yields. Because the preparation cost of the compounds is low, the preparation method according to the present invention can be very efficiently applied particularly for mass-production purpose. Further, for superior cancer cell survival inhibitory effect, dehydrosilybin and apigenin obtained according to the preparation method of the present invention can be efficaciously used as a pharmaceutical composition for prevention or treatment of cancer.

In the preparation method of chromenone derivatives according to the present invention, the above step involves obtaining chromenone compounds, i.e., dehydroxysilybin and apigenin by exposing silybin compound (i.e., chroman compound) in a reactive solvent to radiation.

The reactive solvent may include $C_1$-$C_4$ lower alcohol, and preferably, may include methanol or ethanol containing dimethyl sulfoxide.

To be specific, the reactive solvent may include methanol or ethanol containing 10% dimethyl sulfoxide.

The radiation may be any one selected from a group consisting of gamma radiation, electron radiation and X radiation, and preferably, gamma radiation.

The radiation may be administered at a dose of 100-500 kGy, and preferably, 150-350 kGy.

Problems are expected outside the above-mentioned range, that is, if the radiation dose is below 100 kGy, compounds do not easily form, while above 500 kGy, yield of compound formation decreases.

The above reaction may be processed at a temperature range between 0° and room temperature, and preferably, at room temperature.

To be specific, the compound expressed by formulae 1 and 2 may be obtained by dissolving silybin compound in methanol containing 10% dimethyl sulfoxide, reacting under 150-350 kGy dose of gamma radiation, and after completion of the reaction, passing through column chromatography or vacuum filtration.

The compound expressed by formula 1 or 2, prepared according to the above-explained method, may be available in the form of pharmaceutically acceptable salt, in which the pharmaceutically acceptable salt may advantageously be acid addition salt formed by pharmaceutically acceptable free acid. The acid addition salt may be obtained from inorganic acid such as hydrochloric acid, nitric acid, phosphoric acid, sulfuric acid, hydrobromic acid, hydriodic acid, nitrous acid or phosphorous acid, non-toxic organic acid such as aliphatic mono and dicarboxylate, phenyl-substituted alkanoate, hydroxy alkanoate and alkandioate, aromatic acid, aliphatic and aromatic sulfonic acid, organic acid such as acetic acid, benzoic acid, citric acid, lactic acid, maleic acid, gluconic acid, methane sulfonic acid, 4-toluenesulfonic acid, tartaric acid, fumaric acid. The pharmaceutical non-toxic salt may include sulfate, pyrosulfate, bisulfate, sulfite, bisulfite, nitrate, phosphate, mono-hydrogen phosphate, dihydrogen phosphate, meta phosphate, pyrophosphate chloride, bromide, iodide, fluoride, acetate, propionate, decanoate, caprylate, acrylate, formate, iso-butyrate, caprate, heptanoate, propioleate, oxalate, malonate, succinate, suberate, sebacate, fumarate, maleate, butin-1,4-dioate, hexane-1,6-dioate, benzoate, chloromethyl benzoate, methyl benzoate, dinitro benzoate, hydroxy benzoate, methoxy benzoate, phthalate, terephthalate, benzene sulfonate, toluene sulfonate, chlorobenzene sulfonate, xylene sulfonate, phenyl acetate, phenyl propionate, phenyl butyrate, citrate, lactate, β-hydroxybutyrate, glycol acrylate, maleate, tartrate, methane sulfonate, propanesulfonate, naphthalene-1-sulfonate, naphthalene-2-sulfonate or mandelrate.

The acid addition salt according to the present invention may be prepared by the generally known methods. For example, the compound of formula 1 or 2 is dissolved in organic solvent, such as methanol, ethanol, acetone, methylene chloride, acetonitrile, etc., organic or inorganic acid is added, and the produced precipitate is filtered or dried, or solvent and excess acid is evaporated and then dried, or crystallized in organic solvent.

Pharmaceutically acceptable metallic salt may be prepared using a base. Alkali metal or alkali earth metal salt is obtained by dissolving a compound in an excess of alkali metal hydroxide or alkali earth metal hydroxide solution for example, filtering non-dissolved compound salt, and evaporating and drying the filtrate. In consideration of the limitations, sodium, potassium, or calcium salts may preferably be prepared as the metal salts. Further, corresponding silver salts are obtained by reacting alkali metal or alkali earth metal salts with suitable silver salt (e.g., nitrate).

Furthermore, the present invention includes not only the compound of formula 1 or 2 and pharmaceutically acceptable salt thereof, but also solvate, hydrate which can be prepared therefrom.

Further, the present invention may be advantageously used as a pharmaceutical composition for prevention or treatment of cancer, comprising the compound of formula 1 or 2 prepared by the preparation method explained above, or a pharmaceutically acceptable salt thereof as an effective ingredient.

As a result of measuring cancer cell viability of the compound of formula 1 or 2, superior cancer viability inhibitory effect was observed (see Experimental Example 1, Tables 3 to 8, and FIGS. 2 to 7).

For use as a medicament, the composition comprising the compound of formula 1 or 2 or pharmaceutically acceptable salt thereof as an effective ingredient according to the present invention may be formulated into various dosage forms for oral or parenteral administration and administered in clinical administration, but not limited hereto.

Dosage form for oral administration may include, for example, tablets, pills, hard/soft capsules, liquid, suspension, emulsion, syrup, granule, elixir, or troche, which contains, in addition to effective ingredients, diluents (e.g., lactose, dextrose, sucrose, mannitol, sorbitol, cellulose and/or glycin), lubricant (e.g., silica, talc, stearic acid, and magnesium or calcium salt and/or polyethylene glycol). The tablet may contain binder such as magnesium aluminum silicate, starch paste, gelatin, methyl cellulose, sodium carboxymethyl cellulose and/or polyvinylpyrrolidine, and depending on needs, may include disintegrant such as starch, agar, alginic acid or sodium salt thereof, or boiling mixture and/or absorbent, colorant, flavoring agent, and sweetening agent.

The pharmaceutical composition comprising the compound of formula 1 or 2 as an effective ingredient may be parenterally administered, in which the parenteral administration may include subcutaneous injection, intravenous injection, intramuscular injection, or intrathoracic injection.

For dosage forms for parenteral administration, the compound of formula 1 or 2 or pharmaceutically acceptable salt thereof may be mixed with stabilizer or buffer in water, thus prepared into solution or suspension and packed into ampoule or vial unit for administration. The composition may be sterilized and/or contain preservatives, stabilizers, wettable powder or emulsion accelerator, adjuvant such as salt for osmoregulation and/or buffer, and other therapeutically useful substances, and formulated according to generally known methods including mixing, granulization or coating.

The pharmaceutical composition comprising the compound of formula 1 or 2 as an effective ingredient may be administered into a paten in varying amounts depending on age, weight, gender, form of administration, health condition and severity of disease, and preferably in an amount of 0.01 to 200 mg/kg/day several times a day at predetermined time intervals as determined by a doctor or a pharmacist, and preferably, administered 1 to 3 times a day orally or parenterally.

The examples of the present invention will be explained below. However, because the examples are given only to help elucidate the present invention, the invention is not limited to any specific examples.

Example 1

Preparation of (3,5,7-trihydroxy-2-(3-(4-hydroxy-3-methoxyphenyl)-2-(hydroxymethyl)-2,3-dihydroxy-benzo[b][1,4]dioxin-6-yl)-4H-chroman-4-one (hereinbelow, '2,3-dehydrosilybin') and 5,7-dihydroxy-2-(4-hydroxyphenyl)-4H-chroman-4-one (hereinbelow, 'apigenin')

Compound known as silybin, i.e., 3,5,7-trihydroxy-2-(3-(4-hydroxy-3-methoxyphenyl)-2-(hydroxymethyl)-2,3-dihydroxybenzo[b][1,4]dioxin-6-yl)chroman-4-one (1.0 g) was dissolved in 10 mL dimethylsulfoxide, 90 mL methanol was drop-wise added, slowly stirred, and the reacted solution was irradiated at room temperature by gamma radiation to absorbed dose of 300 kGy. After the reaction, the entire organic layer was collected, dried with sodium sulphate and vacuum concentrated. The reacted mixture was separated with silica gel column chromatography, and target compound (yellow powder, 0.497 g, 49.7%) expressed by formula 1 and target compound (yellow powder 0.426 g, 42.6%) expressed by formula 2 were obtained, respectively.

As a result, the following data was obtained.

TABLE 1

| Compound | Structure | Data |
|---|---|---|
| Target compound 1: (3,5,7-trihydroxy-2-(3-(4-hydroxy-3-methoxyphenyl)-2-(hydroxymethyl)-2,3-dihydroxybenzo[b][1,4]dioxin-6-yl)-4H-chroman-4-one | (structure) | $^1$H-NMR (500 MHz, Acetone-d$^6$) d 3.38 (1H, m, H-11b), 3.58 (1H, m, H-11a), 3.80 (3H, s, 18-OCH$_3$), 4.28 (1H, m, H-12), 4.89 (1H, d, J = 7.5 Hz, H-13), 6.20 (1H, s, H-6), 6.46 (1H, s, H-8), 6.83 (1H, d, J = 8.0 Hz, H-19), 6.89 (1H, d, J = 7.5 Hz, H-16), 7.05 (1H, s, H-15), 7.12 (1H, d, J = 8.5 Hz, H-5'), 7.77 (2H, s, H-2', H-6'), 12.4 (s, 5-OH); HREIMS calcd for $C_{25}H_{20}O_{10}$ (M$^+$) 480.1056; found, 480.1057. |
| Target compound 2: 5,7-dihydroxy-2-(4-hydroxyphenyl)-4H-chroman-4-one | (structure) | $^1$H-NMR (500 MHz, Acetone-d$^6$) d 6.19 (1H, s, H-8), 6.48 (1H, s, H-6), 6.76 (1H, s, H-3), 6.93 (2H, d, J = 8.0 Hz, H-3', H-5'), 7.91 (2H, d, J = 8.0 Hz, H-2', H-6'), 12.9 (s, 5-OH); HREIMS calcd for $C_{15}H_{10}O_5$ (M$^+$) 270.0528; found, 270.0529. |

Examples 2 to 6

Measurement of Changes in Reagent Content Depending on Dose of Gamma Radiation

Experiments were carried out to measure transformation rates of dehydrosilybin and apigenin compounds according to the radiation dose on the starting substance, i.e., on silybin, in the same manner as in Example 1, except for using radiation dose of 300 kGy.

As a result, the following data was obtained.

TABLE 2

| | tR (min) | Ex. 2 50 kGy Area (%) | Ex. 3 70 kGy Area (%) | Ex. 4 100 kGy Area (%) | Ex. 5 150 kGy Area (%) | Ex. 6 200 kGy Area (%) | Ex. 1 300 kGy Area (%) |
|---|---|---|---|---|---|---|---|
| Starting substance (Silybin) | 28.55 | 31.58 | 28.79 | 25.13 | 19.45 | 15.913 | 7.562 |
| | 28.73 | 37.31 | 35.99 | 31.04 | 21.70 | 19.357 | 9.130 |
| Product 1 (Dehydrosilybin) | 31.80 | 3.15 | 4.74 | 6.69 | 10.01 | 17.554 | 23.114 |
| | 32.00 | 5.53 | 6.68 | 8.79 | 14.13 | 17.040 | 26.652 |
| Product 2 (Apigenin) | 30.49 | 22.49 | 23.79 | 28.36 | 34.70 | 30.135 | 33.541 |

Referring to Table 2, silybin decreased as the radiation dose on silybin increased, while the fractions of compounds of formulae 1 and 2 increased as the radiation dose increased.

Accordingly, because the amount of target compounds increases as the radiation dose increases, the preparation method according to the present invention can be advantageously used for fabricating dehydrosilybin and apigenin compounds.

Experimental Example 1

Anticancer Effect Measurement

To investigate the cancer cell inhibitory effect of the compounds of formulae 1 and 2 obtained by the preparation method according to the present invention, experiment was conducted.

EZ-Cytox cell viability assay kit (Daeil Lab, Korea) was used to measure cancer cell growth inhibitory activity, and prostate carcinoma cell line (DU145), cervical carcinoma cell line (Hela), colon carcinoma cell line (SW480), and lung carcinoma cell line (H460) were used for cancer cells.

All the cancer cells were incubated in 96-well plate at concentration of $5 \times 10^4$ cells/mL. After 24 h, dehydrosilybin compound of formula 1 and apigenin compound of formula 2 according to the present invention, and starting substance (i.e., silybin) as a control were treated at concentration of 50 μg/mL. After culturing at 37° C., 5% carbon dioxide environment, 24 h, 10 μL of kit solution was treated in each well. After 3 h of additional culturing, the optical absorbance was measured at 480 nm. The result is listed in Tables 3 to 6 and illustrated in FIGS. 2 to 7.

TABLE 3

Anticancer effect on prostate carcinoma cell line (DU145)

| Compound | Cell viability (%) |
| --- | --- |
| Compound of Formula 1 | 40.4 |
| Compound of formula 2 | 51.6 |
| Control (silybin) | 87.9 |
| Non-treated | 100 |

Figure 2:
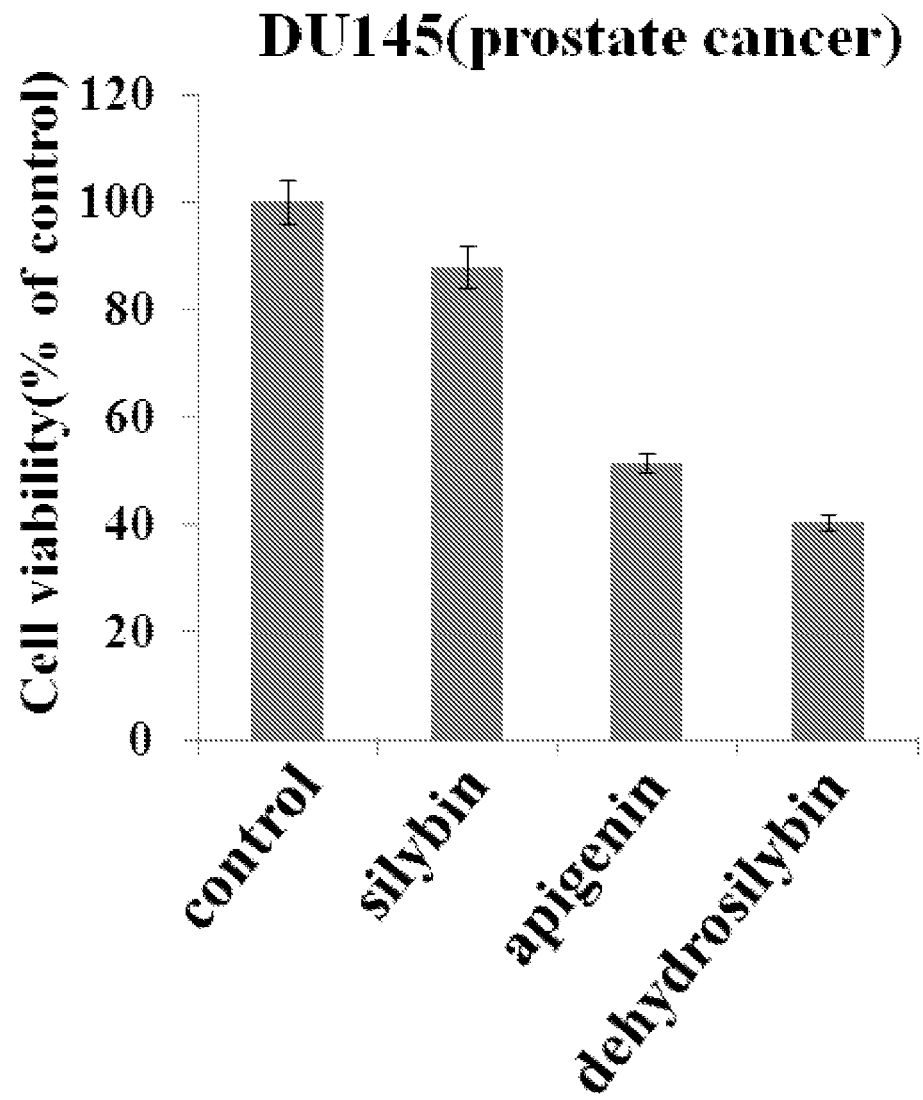
FIG. 2 illustrates cell viability of prostate carcinoma cell line (DU145) of compounds according to an embodiment of the present invention.

Referring to Table 3, the prostate cell viability was 40.4% and 51.6% respectively, with respect to the compounds of formulae 1 and 2 obtained by the preparation method according to the present invention, which were four to five times superior to that (87.9%) of the starting substance (i.e., silybin, control). As a result, it was confirmed that the compounds of formulae 1 and 2 had good apoptotic effect on prostate carcinoma cells (FIG. 2).

TABLE 4

Anticancer effect on cervical carcinoma cell line (Hela)

| Compound | Cell viability (%) |
| --- | --- |
| Compound of formula 1 | 21.1% |
| Compound of formula 2 | 38.7% |
| Control (silybin) | 83.2% |
| Non-treated | 100 |

Figure 3:
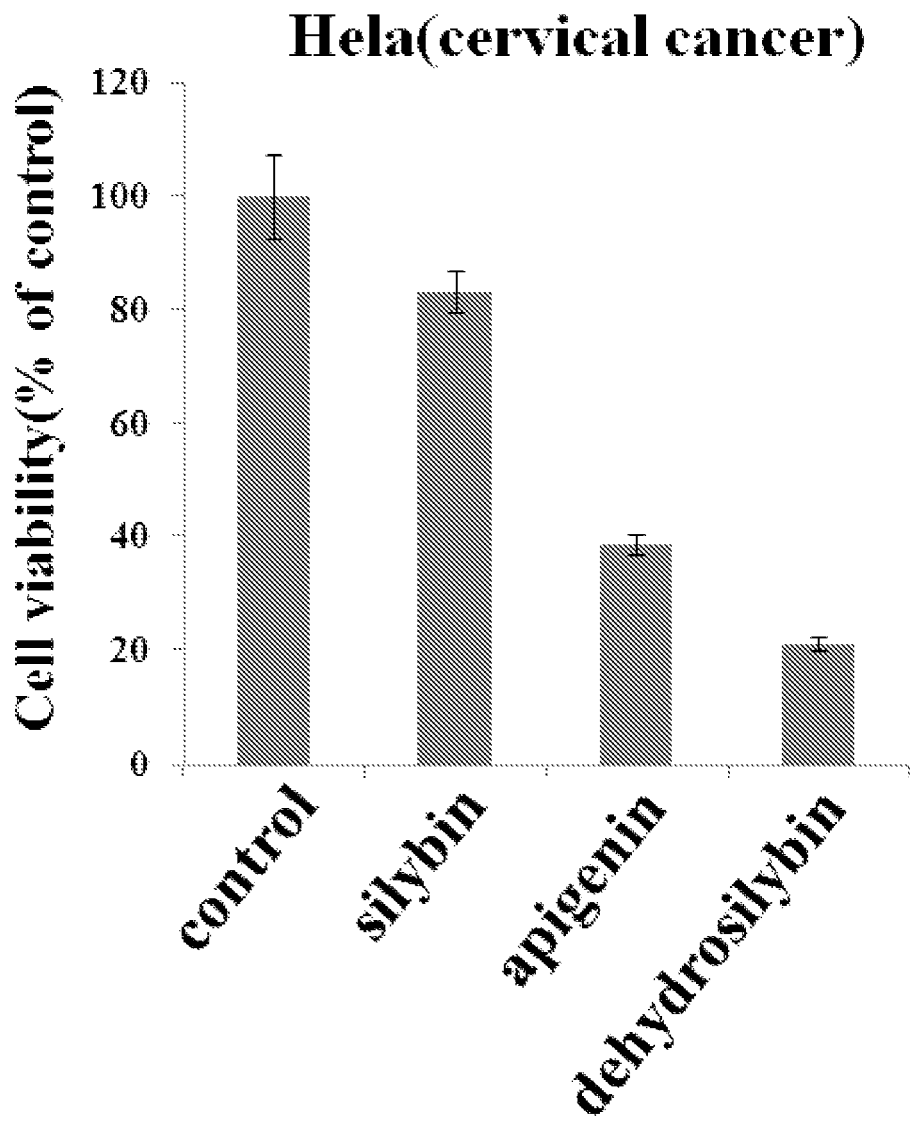
FIG. 3 illustrates cell viability of cervical carcinoma cell line (Hela) of compounds according to an embodiment of the present invention.

Referring to Table 4, the cervical cancer cell viability was 21.1% and 38.7% respectively, with respect to the compounds of formulae 1 and 2 obtained by the preparation method according to the present invention, which were 3.6 to 4.7 times superior to that (83.2%) of the starting substance (i.e., silybin, control). As a result, it was confirmed that the compounds of formulae 1 and 2 had good apoptotic effect on prostate carcinoma cells (FIG. 3).

TABLE 5

Anticancer effect on colon carcinoma cell line (SW480)

| Compound | Cell viability (%) |
| --- | --- |
| Compound of formula 1 | 41.7% |
| Compound of formula 2 | 49.2% |
| Control (silybin) | 79.8% |
| Non-treated | 100 |

Figure 4:
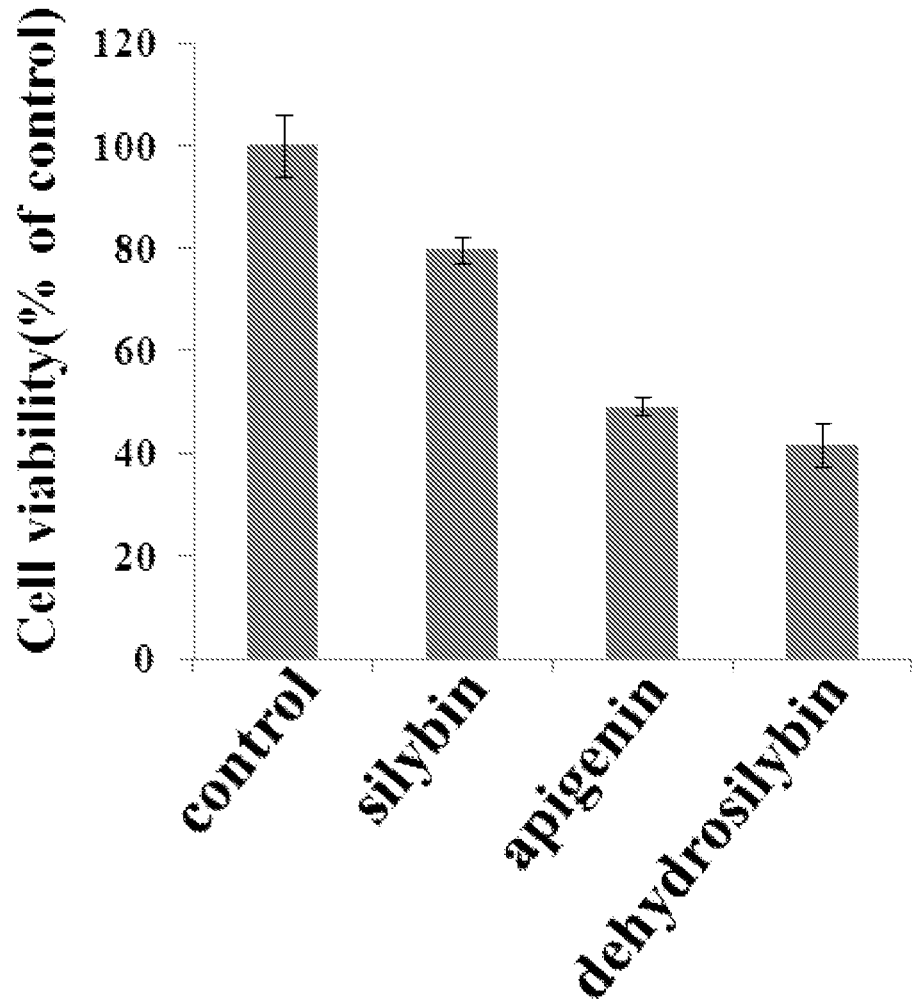
FIG. 4 illustrates cell viability of colon carcinoma cell line (SW480) of compounds according to an embodiment of the present invention.

Referring to Table 5, the colon cancer cell viability was 41.7% and 49.2% respectively, with respect to the compounds of formulae 1 and 2 obtained by the preparation method according to the present invention, which were 2.5 to 2.9 times superior to that (79.8%) of the starting substance (i.e., silybin, control). As a result, it was confirmed that the compounds of formulae 1 and 2 had good apoptotic effect on colon carcinoma cells (FIG. 4).

TABLE 6

Anticancer effect on lung carcinoma cell line (H460)

| Compound | Cell viability (%) |
| --- | --- |
| Compound of formula 1 | 66.3% |
| Compound of formula 2 | 97.4% |
| Control (silybin) | 101% |
| Non-treated | 100 |

Figure 5:
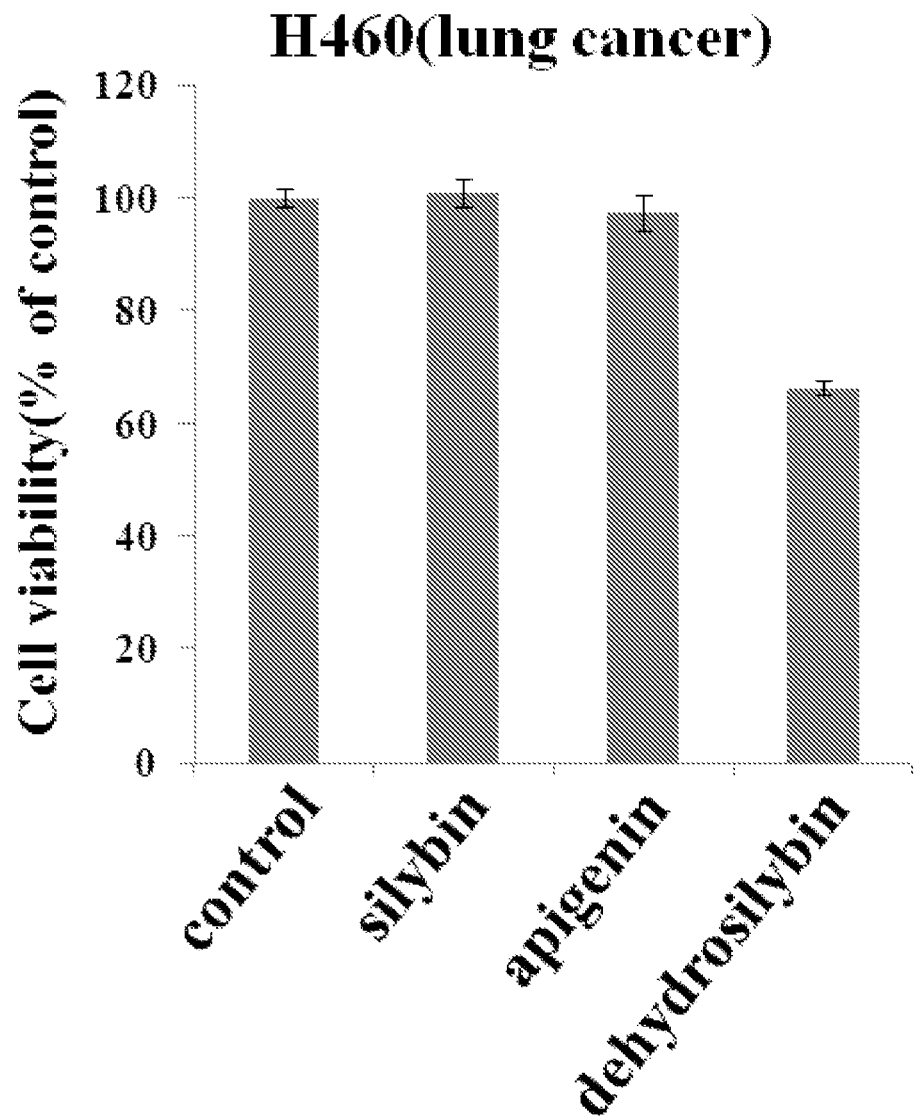
FIG. 5 illustrates cell viability of lung carcinoma cell line (H460) of compounds according to an embodiment of the present invention.

Referring to Table 6, the lung cancer cell viability was 66.3% and 97.4% respectively, with respect to the compounds of formulae 1 and 2 obtained by the preparation method according to the present invention, which were 2.6 to 3.3 times superior to that (101%) of the starting substance (i.e., silybin, control). As a result, it was confirmed that the compounds of formulae 1 and 2 had good apoptotic effect on lung carcinoma cells (FIG. 5).

TABLE 7

Anticancer effect on colon carcinoma cell line (SW620)

| Compound | Cell viability (%) |
| --- | --- |
| Compound of formula 1 | 27.8% |
| Compound of formula 2 | 39.4% |
| Control (silybin) | 75.5% |
| Non-treated | 100 |

Figure 6:
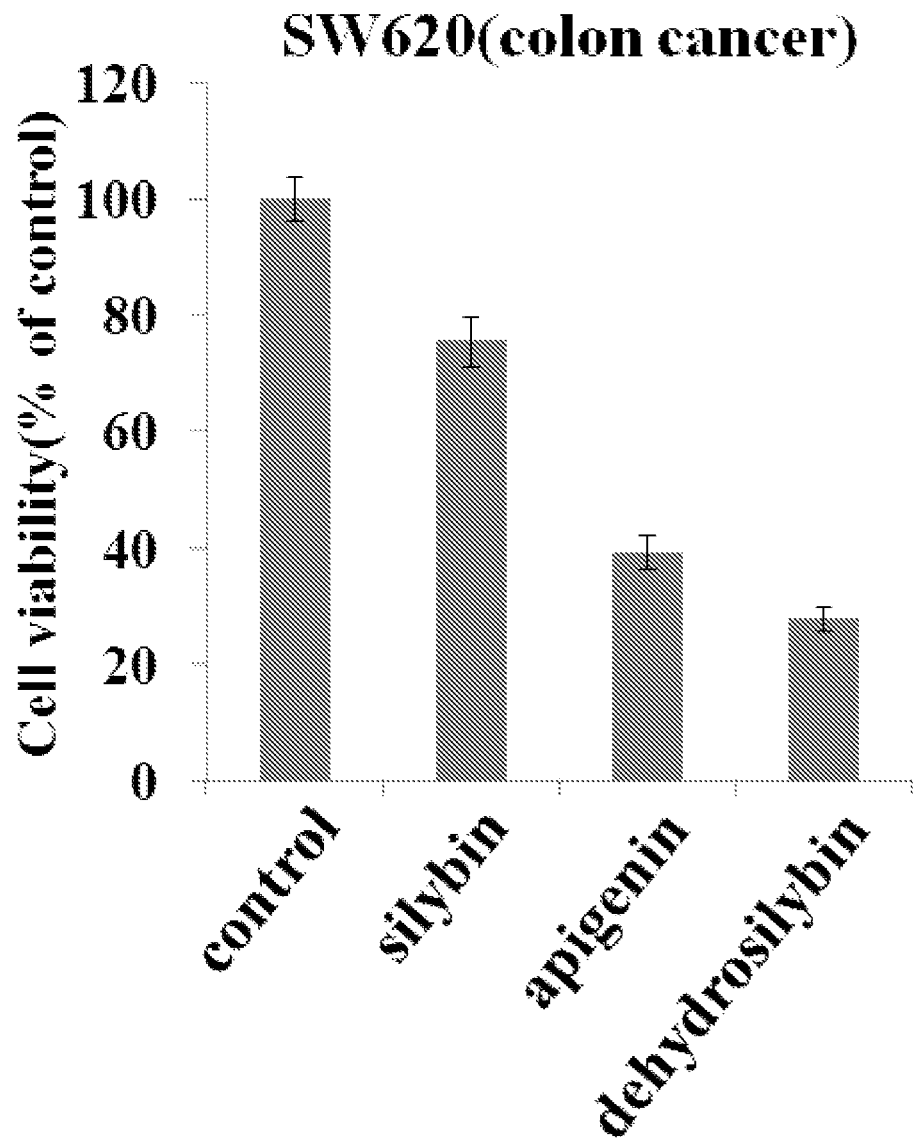
FIG. 6 illustrates cell viability of colon carcinoma cell line (SW620) of compounds according to an embodiment of the present invention.

Referring to Table 7, the colon cancer cell viability was 27.8% and 39.4% respectively, with respect to the compounds of formulae 1 and 2 obtained by the preparation method according to the present invention, which were 2.5 to 2.9 times superior to that (75.5%) of the starting substance (i.e., silybin, control). As a result, it was confirmed that the compounds of formulae 1 and 2 had good apoptotic effect on colon carcinoma cells (FIG. 6).

TABLE 8

Anticancer effect on lung carcinoma cell line (A549)

| Compound | Cell viability (%) |
| --- | --- |
| Compound of formula 1 | 58.9% |
| Compound of formula 2 | 72.1% |
| Control (silybin) | 97.5% |
| Non-treated | 100 |

Figure 7:
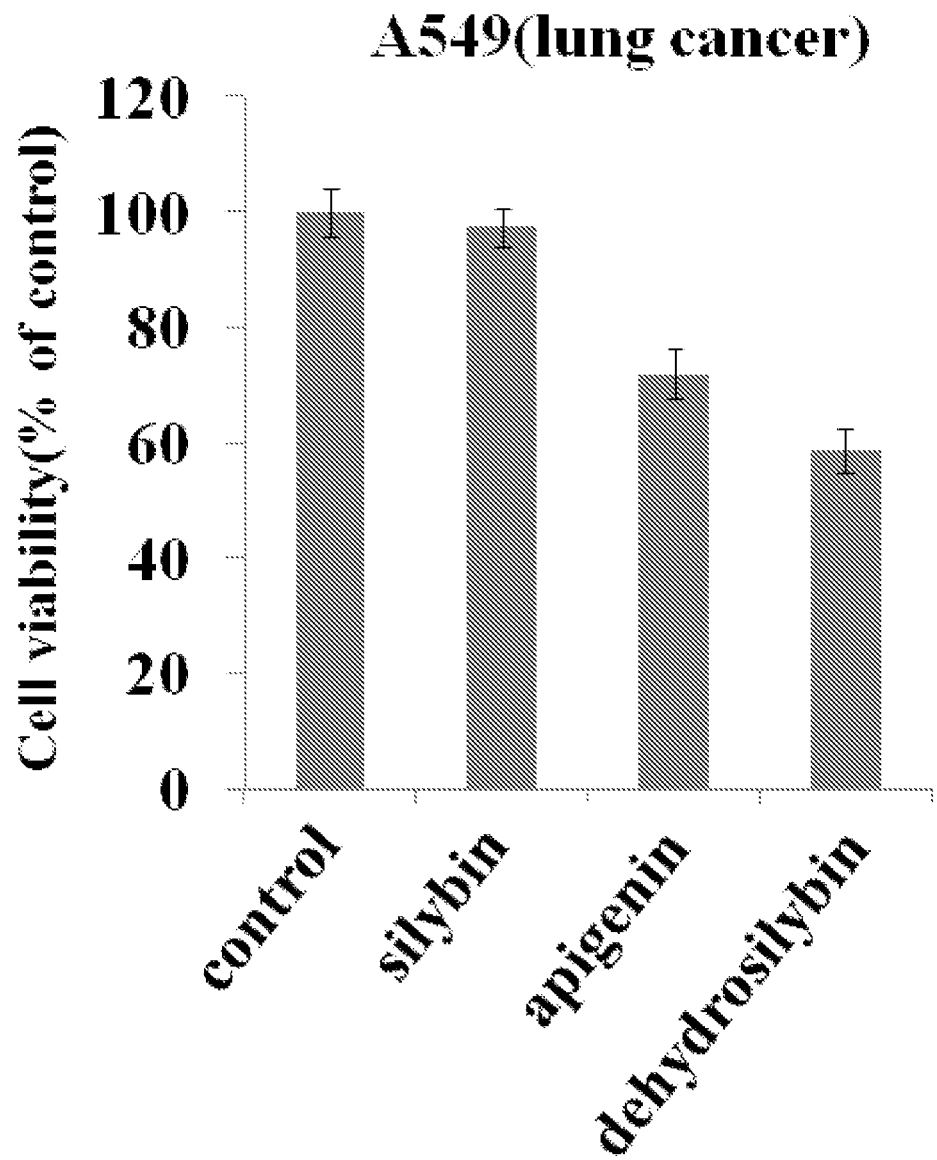
FIG. 7 illustrates cell viability of lung carcinoma cell line (A549) of compounds according to an embodiment of the present invention.

Referring to Table 8, the lung cancer cell viability was 58.9% and 72.1% respectively, with respect to the compounds of formulae 1 and 2 obtained by the preparation method according to the present invention, which were 11.2 to 16.4 times superior to that (97.5%) of the starting substance (i.e., silybin, control). As a result, it was confirmed that the compounds of formulae 1 and 2 had good apoptotic effect on lung carcinoma cells (FIG. 7).

Accordingly, compared to a conventional synthesis method, it is possible to prepare dehydrosilybin and apigenin in a simpler process and with higher yield according to the preparation method according to the present invention. Further, in consideration of good cancer cell apoptotic effect thereof, dehydrosilybin and apigenin prepared according to the present invention can be advantageously used as an anticancer composition.

Meanwhile, the compounds expressed by formula 1 or 2 according to the present invention may be formulated into a variety of dosage forms as in the following examples. However, while the examples provided below describe some of the dosage forms containing the compounds of formula 1 or 2 according to the present invention, the present invention is not limited to any of specific examples.

Preparative Example 1

Preparation of Powder

| | |
|---|---|
| Compound of formula 1 or 2 | 2 g |
| Lactose | 1 g |

A powder was prepared by mixing the above components and filling them into an airtight bag.

Preparative Example 2

Preparation of Tablet

| | |
|---|---|
| Compound of formula 1 or 2 | 100 mg |
| Corn Starch | 100 mg |
| Lactose | 100 mg |
| Magnesium Stearate | 2 mg |

A tablet was prepared by mixing the above components and tabletting them with a preparation method of a conventional tablet.

Preparative Example 3

Preparation of Capsule

| | |
|---|---|
| Compound of formula 1 or 2 | 100 mg |
| Corn Starch | 100 mg |
| Lactose | 100 mg |
| Magnesium Stearate | 2 mg |

A capsule was prepared by mixing the above components and filling them into a gelatin capsule with a preparation method of a conventional capsule.

Preparative Example 4

Preparation of Injection

| | |
|---|---|
| Compound of formula 1 or 2 | 100 mg |
| Mannitol | 180 mg |
| $Na_2HPO_4 \cdot 2H_2O$ | 26 mg |
| Distilled water | 2974 mg |

The injection was prepared, containing above-indicated contents of the components according to general known preparation method of injection.

While the present invention has been particularly shown and described with reference to exemplary embodiments thereof, it will be understood by those skilled in the art that various changes in form and details may be made therein without departing from the spirit and scope of the invention as defined by the appended claims.

[Reaction Formula 1]
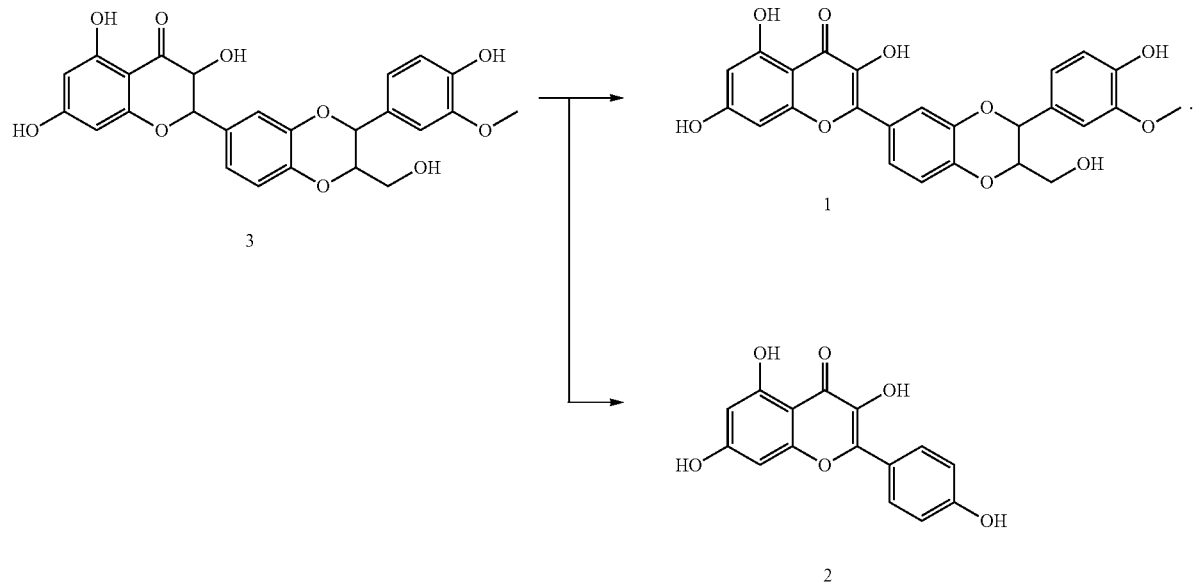

What is claimed is:

1. A preparation method of compounds of chemical formula 1 and 2 as expressed by Reaction Formula 1, comprising:
   a) dissolving a compound of chemical formula 3 in a reaction solvent;
   b) exposing the dissolved compound of chemical formula 3 to radiation to obtain the compounds of both chemical formula 1 and 2; and
   c) isolating the compounds of both chemical formula 1 and 2,

[Reaction Formula 1]

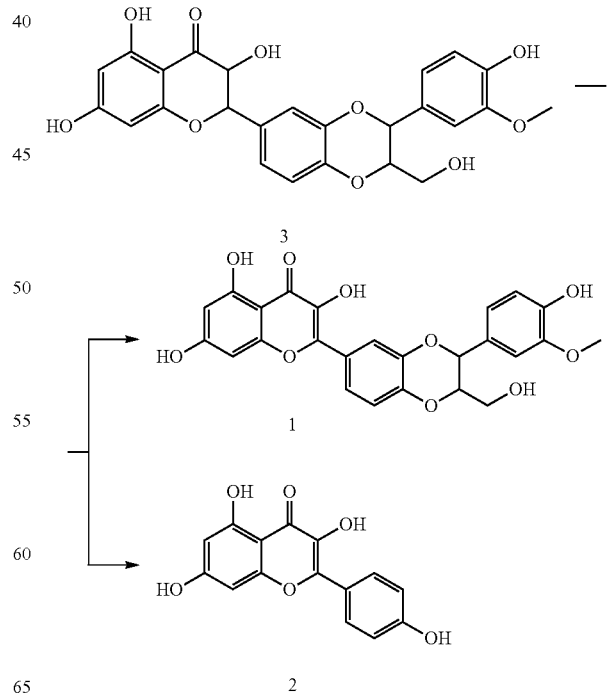

2. The preparation method as set forth in claim 1, wherein the reaction solvent comprises $C_1$-$C_4$ lower alcohol containing dimethyl sulfoxide.

3. The preparation method as set forth in claim 1, wherein the reaction solvent comprises methanol or ethanol containing dimethyl sulfoxide.

4. The preparation method as set forth in claim 1, wherein the radiation is selected from the group consisting of gamma radiation, electron radiation and X radiation.

5. The preparation method as set forth in claim 1, wherein the radiation is emitted at a dose of 100-500 kGy.

6. The preparation method as set forth in claim 1, wherein the step of exposing the dissolved compound of chemical formula 3 to radiation is performed at a temperature ranging between 0° C. and room temperature.

7. The preparation method as set forth in claim 1, wherein said isolating step comprises isolating the compounds of both chemical formula 1 and 2 using column chromatography or vacuum filtration.

8. The preparation method as set forth in claim 1, wherein said isolating step comprises isolating the compound of chemical formula 1 or 2 in a form of a pharmaceutically acceptable salt thereof.

9. The preparation method as set forth in claim 1, wherein the reaction solvent comprises methanol containing about 10% of dimethyl sulfoxide by volume.

10. The preparation method as set forth in claim 9, wherein the radiation is emitted at a dose of 100-500 kGy.

11. A preparation method of compounds of chemical formula 1 and 2 as expressed by Reaction Formula 1, comprising:
 a) dissolving a compound of chemical formula 3 in a reaction solvent;
 b) exposing the dissolved compound of chemical formula 3 to radiation to obtain the compounds of both chemical formula 1 and 2; and
 c) isolating the compounds of both chemical formula 1 and 2, wherein the reaction solvent comprises methanol containing dimethyl sulfoxide

[Reaction Formula 1]

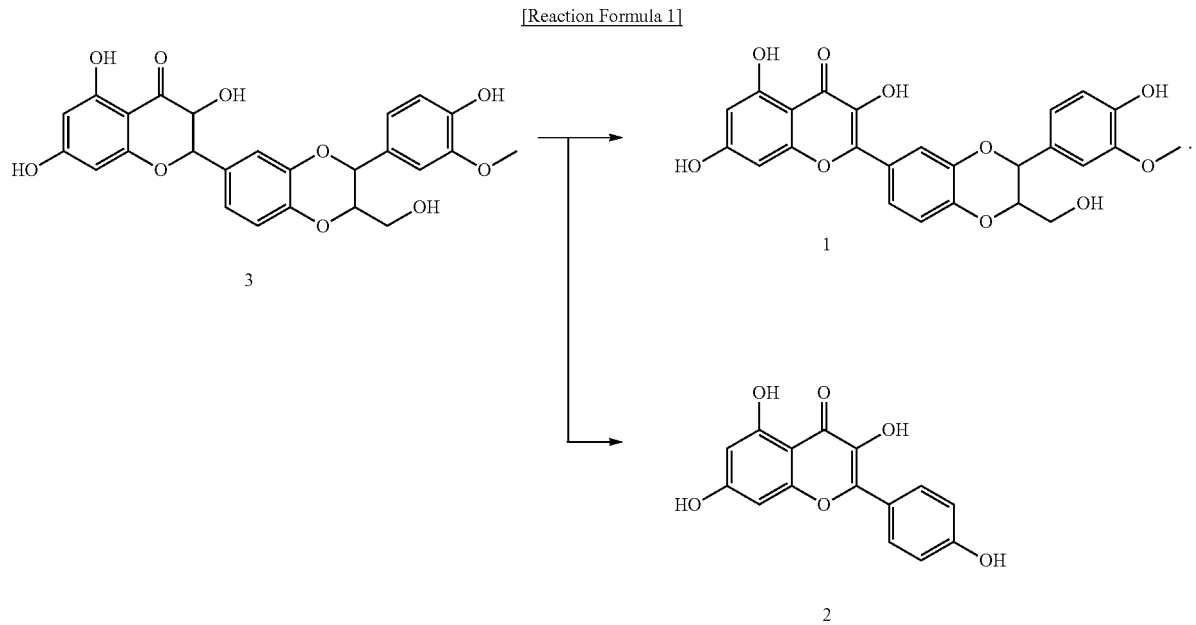 [SMILES: COc1cc(C2Oc3cc(C4Oc5cc(O)cc(O)c5C(=O)C4O)ccc3OC2CO)ccc1O ; COc1cc(C2Oc3cc(-c4oc5cc(O)cc(O)c5c(=O)c4O)ccc3OC2CO)ccc1O ; O=c1c(O)c(-c2ccc(O)cc2)oc2cc(O)cc(O)c12]

12. The preparation method as set forth in claim 11, wherein the reaction solvent comprises methanol containing about 10% of dimethyl sulfoxide by volume.

13. A preparation method of compounds of chemical formula 1 and 2 as expressed by Reaction Formula 1, comprising:
 a) dissolving a compound of chemical formula 3 in a reaction solvent;
 b) exposing the dissolved compound of chemical formula 3 to radiation to obtain the compounds of both chemical formula 1 and 2; and
 c) isolating the compounds of both chemical formula 1 and 2 from the compound of chemical formula 3 after the exposure step,